(12) United States Patent
Payne et al.

(10) Patent No.: US 9,974,562 B2
(45) Date of Patent: May 22, 2018

(54) RIGID ELASTIC BENT TOOL FOR LAPAROSCOPIC SURGERY

(71) Applicant: OmniGuide, Inc., Cambridge, MA (US)

(72) Inventors: Robert Payne, Wellesley, MA (US); Jesse Rusk, Allston, MA (US); Mihai Ibanescu, Somerville, MA (US); Crystal Simon, San Jose, CA (US)

(73) Assignee: OmniGuide, Inc., Cambridge, MA (US)

( * ) Notice: Subject to any disclaimer, the term of this patent is extended or adjusted under 35 U.S.C. 154(b) by 85 days.

(21) Appl. No.: 14/210,793

(22) Filed: Mar. 14, 2014

(65) Prior Publication Data

US 2014/0316384 A1 Oct. 23, 2014
US 2017/0296226 A9 Oct. 19, 2017

Related U.S. Application Data

(60) Provisional application No. 61/789,448, filed on Mar. 15, 2013, provisional application No. 61/813,517, filed on Apr. 18, 2013.

(51) Int. Cl.
*A61B 17/00* (2006.01)
*A61B 17/34* (2006.01)
*A61B 18/14* (2006.01)
*A61B 90/00* (2016.01)

(52) U.S. Cl.
CPC ...... *A61B 17/3421* (2013.01); *A61B 18/1482* (2013.01); *A61B 18/1487* (2013.01); *A61B 2017/00292* (2013.01); *A61B 2017/00845* (2013.01); *A61B 2017/00862* (2013.01); *A61B 2090/0817* (2016.02)

(58) Field of Classification Search
CPC ............ A61B 17/3421; A61B 18/1482; A61B 18/1487; A61B 2017/00292; A61B 2017/00862; A61B 18/22; A61B 18/24
USPC ............................................ 606/1, 2, 13–16
See application file for complete search history.

(56) References Cited

U.S. PATENT DOCUMENTS 5,127,393 A * 7/1992 McFarlin ........... A61B 1/00154
600/114
6,190,353 B1 * 2/2001 Makower ............. A61B 1/3137
600/137

(Continued)

*Primary Examiner* — John R Downey
(74) *Attorney, Agent, or Firm* — Seed Intellectual Property Law Group LLP

(57) ABSTRACT

A surgical tool and method of use during laparascopic surgery, the tool including a shaft having a distal region with an elastic modulus E. Distal and proximal regions of the shaft have outer diameters $D_1$ and $D_2$ respectively, with $D_2 > D_1$. The distal region has a bend and terminates in a working feature having a distal end. The distal region has a length L1 measured in a direction parallel to the shaft axis in the proximal region, and has an offset $d_{off}$ relative to the proximal region where $d_{off} > D_2$. The elastic modulus E and the length of L1 are selected so that the working feature is insertable through an access device yet the distal region does not deflect noticeably when a force of 10 N is applied perpendicular to the distal end of the working feature.

29 Claims, 10 Drawing Sheets

(56) References Cited

U.S. PATENT DOCUMENTS

| | | | | |
|---|---|---|---|---|
| 6,228,023 B1* | 5/2001 | Zaslavsky | ............ | A61B 17/221 |
| | | | | 600/204 |
| 6,238,393 B1* | 5/2001 | Mulier | ............... | A61B 18/1482 |
| | | | | 606/41 |
| 2004/0158136 A1* | 8/2004 | Gough | ............... | A61B 5/14546 |
| | | | | 600/328 |
| 2005/0187537 A1* | 8/2005 | Loeb | ................ | A61B 17/32002 |
| | | | | 606/1 |
| 2007/0179340 A1* | 8/2007 | Jorgensen | ................ | A61B 1/04 |
| | | | | 600/139 |
| 2009/0317760 A1* | 12/2009 | Gadbois | ............... | A61C 17/043 |
| | | | | 433/91 |

\* cited by examiner

RIGID ELASTIC BENT TOOL FOR LAPAROSCOPIC SURGERY

CROSS-REFERENCE TO RELATED APPLICATION

This application claims priority to U.S. Provisional Application No. 61/789,448 filed 15 Mar. 2013 and to U.S. Provisional Application No. 61/813,517 filed 18 Apr. 2013.

FIELD OF THE INVENTION

This invention relates to surgical tools for laparoscopic surgery and more particularly to bent tools such probes, electrosurgical devices, and waveguide conduits that are insertable through access devices such as trocars.

BACKGROUND OF THE INVENTION

There is a trend toward less invasive surgical procedures performed by introducing small diameter, flexible tools into natural body openings and small incisions. These tools can enable tissue visualization, imaging, analysis, manipulation, cutting, coagulation, and removal. An example of a procedure done through a natural body opening is polyp visualization and removal during a colonoscopy. Examples of procedures done through one or more small incisions utilizing access devices such as trocars include laparoscopic hysterectomy or cholecystectomy. Laparoscopic incisions are typically 3 mm to 15 mm in diameter. Some procedures can be done through incisions 3 mm or smaller, and have been called "needlescopic".

One type of laparascopic surgery is single incision laparascopic surgery, where a multiport trocar is used to introduce a cluster of surgical tools. Incisions that start from an instrument already in a natural body opening, called natural orifice transluminal endoscopic surgery ("NOTES"), are a topic of current surgical research, as are various percutaneous procedures. Examples include NOTES cholicystectomy.

Referring to FIG. 1, traditional laparascopic tooling 100 typically includes a long, small diameter rigid shaft 110 with a working feature 120 located on the distal end, and a hand grip 130 located proximally. The shaft 110 is commonly stainless steel with an outer diameter $D_2$ being an industry standard size, commonly 3 mm, 5 mm, or 8 mm.

Referring to FIG. 2, these specific laparascopic shaft sizes are desirable due to the need for the tool to pass through an opening of an access device such as a trocar 200 typically used in minimally invasive procedures and having a similar size. For example, trocars with inner diameter openings $D_3$ of approximately 4 mm, 6 mm, and 9 mm may be used with 3 mm, 5 mm, and 8 mm tools, respectively. A laparascopic trocar 200 typically includes a sleeve or cannula 210 and a sealing orifice within a seal housing 220. The seal housing 220 typically includes a relief valve 230, also utilized for insufflation gases. Sealing orifices are designed to maintain pressure in the abdomen during laparascopic surgery, and may also utilize a duckbill type of elastomeric check valve, in which pressure on the high pressure side of the seal helps maintain closure.

Trocar sleeve lengths vary, with typical lengths ranging from 7 cm to 15 cm. The term "trocar" is utilized broadly herein to include a tubular cannula or sleeve with proximal seal housing through which sharp-tipped or blunt instruments are insertable, such as disclosed in the following U.S. Pat. Nos. 5,385,553; 5,792,112; 5,803,919; and 6,217,555 by Hart et al.

Long, thin, flexible waveguides are well adapted for performing the procedures described above, and suit the current growing interest in and use of laser surgery. Generally, waveguides may be strengthened and protected by additional elements on the outside, such as jackets, and may have additional elements that add functionality, such as distal tips. Waveguides disposed inside protective jackets and having additional functionality elements are often referred to as waveguide assemblies.

For further mechanical strength and manipulation, it may be desirable to place waveguides or waveguide assemblies inside other mechanical structures, e.g., waveguide conduits, which may provide protection, strength, and structure for surgical access control.

Waveguide conduits are typically placed on waveguides or waveguide assemblies after manufacturing or assembly of the waveguides, generally at point of use. Waveguide conduits can be either flexible or rigid, or have a rigid portion and a flexible portion. A waveguide conduit can have multiple functions. A primary and important function of the waveguide conduits is to give a user control of surgical access, in either a hand-held manner, known as handpiece style waveguide conduits, or by means of electromechanical actuators or robotic devices such as Flexguide™ products available from OmniGuide, Inc., based in Cambridge, Mass.

Examples of known robotic surgical systems utilizing lasers and other instruments are provided by Mohr in U.S. Patent Publication No. 2009/0171372, by Williams et al. in U.S. Patent Publication No. 2009/0248041 and by Prisco et al. in U.S. Patent Publication No. 2010/0249507, for example, all assigned to Intuitive Surgical Operations, Inc. and/or Intuitive Surgical, Inc. of Sunnyvale, Calif., which provides the Da Vinci™ robotic platform. Robotically assisted surgery through a single port utilizing an image capturing device and multiple surgical tools is described by Mohr in U.S. Pat. No. 8,517,933.

Other functional elements may include mechanical protection of the waveguide, control of waveguide bending for surgical access and control of associated optical performance variation (optical loss due to bends) of the waveguide, means for keeping the waveguide inside the waveguide conduit and optically aligned with the conduit distal tips during usage, couplers for mechanical coupling of the waveguide conduit with an external manipulator, and mechanical supports of other functional elements that may be affixed to the conduit (e.g., distal tips, suction irrigation tools, etc.). The waveguide conduit is preferably steerable in a well-controlled and precise motion manner, critical for minimally invasive surgical procedures, by means of a handle and/or attachment to a manipulator. It is preferably sterilizable and may be disposable or reusable.

Suitable materials for the waveguide conduit portions include stainless steel (e.g., 300 and 400 series surgical grade steels), titanium, aluminum, various alloys of aluminum, ceramic materials such as alumina and zirconia, and polymer materials such as silicones, polyamides, polycarbonates, PEEK, and polyolefin.

The configuration of the waveguide conduit depends on the particular application. It may vary in length and may contain several bends placed anywhere between distal (adjacent to the surgical site) and proximal ends (closer to the surgeon or other user of the device), depending on the requirements of a particular application. For example, conduits used for oral surgeries (e.g., base of tongue), are generally rigid and relatively short with fewer bends than waveguide conduits used for laryngeal work. A typical range of bend angles between distal and proximal ends is 20°-60° and total length may be from about 5 cm to about 25 cm for oral surgeries, while for laryngeal surgical procedures the bend angles maybe larger, up to 90°, and the total length may be up to about 45 cm. Yet for laparascopic procedures, even longer waveguide conduits are utilized, up to about 65 cm.

More generally, several conventional approaches are typically employed to provide a surgical tool that i) has a bend, ii) can be inserted into a trocar iii) without having to push too hard to get it through the trocar, and iv) does not deflect too much when used during surgical procedures.

In one prior approach, one may utilize an angled working feature that is limited to an overall diameter that is not larger than the inner diameter ("I.D.") of the trocar sleeve. There is typically 1 mm clearance between the I.D. of the trocar sleeve and the outer diameter ("O.D.") of the tool shaft, or 0.5 mm of clearance surrounding the shaft when it is centered in the trocar sleeve, though the exact clearance varies from manufacturer to manufacturer. As mentioned above, for example, 3 mm, 5 mm, and 8 mm shafts are typically used with 4 mm, 6 mm, and 9 mm trocar sleeve dimensions, respectively. This may result in a limited working angle that is achievable.

Other prior solution includes altering the angle of the working feature after insertion through the trocar sleeve, either through articulation utilizing steerable linkages or shape memory alloys. These solutions may be costly, adversely affect the robustness of the tool, and introduce cleaning and sterilization complications.

It is desirable to have surgical tools such as waveguide conduits that hold a selected bend during normal surgical use yet can be passed through trocars and other access devices.

SUMMARY OF THE INVENTION

An object of the present invention is provide an improved surgical tool with a working feature having a bend that can be inserted through an access device such as a trocar.

Another object of the present invention is to provide such a tool, and method of using same, that yields sufficiently to pass through the access device yet holds its bend during normal use.

This invention features a non-articulating, bent surgical tool suitable for use during laparascopic surgery and capable of insertion through an access device during surgery. The tool includes a shaft having a longitudinal axis extending along at least a proximal region with diameter $D_2$, a distal region with a diameter $D_1$ and having an elastic modulus E, with diameter $D_2$ greater than diameter $D_1$. The distal region terminates in a working feature having a distal end. The shaft defines a bend in the distal region, the bend having a bend radius R, a bend angle $\Theta$, and a length after the bend $L_{ab}$. The distal region has a length L1 measured in a direction parallel to the shaft longitudinal axis, the distal region having an offset $d_{off}$ relative to the proximal region where $d_{off}$ is greater than $D_2$, and the bend angle $\Theta$ is greater than 10 degrees. The elastic modulus E and the length L1 are selected so that the working feature is insertable through the access device yet the distal region deflects less than 1 mm when a force of 10 N is applied perpendicular to the distal end of the working feature.

In certain embodiments, $d_{off} > 1.5\ D_2$, more preferably, $d_{off} > 2\ D_2$. In some embodiments, the bend angle $\Theta$ is greater than 10 degrees, more preferably between 15 and 45 degrees. The length after the bend $L_{ab}$ preferably is between 0 mm and 25 mm. In some embodiments, the bend is substantially retained during the advancement of the tool through the trocar, for example, at least 30% of the bend may be retained during the advancement of the tool through the trocar.

This invention also features a method for performing laparascopic surgery including selecting and then inserting a tool having an offset $d_{off}$, as defined herein, into a trocar, having an inner diameter $D_3$, with $d_{off}$ being at least 1.1 times as large as $D_3$, the insertion being accomplished using less than 10 N of force. During insertion, the distal region typically straightens enough to pass through the sleeve, but retains a bend.

One method for designing a surgical tool includes selecting a trocar having an inner diameter $D_3$. The surgical tool has at least two diameters $D_1$ and $D_2$, associated respectively with distal and proximal regions, having lengths L1 and L2, respectively. The distal region has an elastic modulus E, with $D_3-D_2$ typically being less than 1 mm. The tool has a desired offset $d_{off}$, a desired bend angle $\Theta$, a bend radius R, and a material with a predetermined elastic modulus. A maximum (i.e., a force no greater than a predetermined amount) required force is selected for inserting the tool into the trocar with inner diameter $D_3$. The maximum $L_{ab}$ and/or maximum bend angle are also selected.

In an aspect, a bend is defined in a portion of the distal region defining an offset $d_{off}$ between a distal tip of the shaft and an extension of a top surface of the proximal region, the top surface being a surface of the proximal region farthest from the distal tip. In one embodiment, at least the bend portion of the distal tip includes an elastic material.

One or more of the following features are included in certain embodiments. The elastic material includes at least one metal, metal alloys, and/or glass. The offset $d_{off}$ may be measured perpendicularly between a first and a second parallel line, the first line including a distal tip of the shaft and the second line extending along the top surface of the proximal region. In some embodiments, at least one of the distal region and the proximal region of the longitudinal shaft defines at least one lumen. The distal region and proximal region of the longitudinal shaft may define at least two lumens. In a number of embodiments, a waveguide is passable through at least one lumen.

The elastic material may be adapted to permit passage of the distal region through a trocar having an inner diameter $D_3$ less than the offset $d_{off}$. A force of less than about 10 N may be required to advance the shaft through the trocar. The diameter $D_2$ of the proximal region may have a sliding fit with the trocar. In one embodiment, a ratio of (a difference in an inner diameter $D_3$ of the trocar and the outer diameter $D_2$ of the proximal region)/$D_2$ is selected from a range of 10% to 30%.

A bend angle $\theta$ of the bend may be selected from a range of 15° to 45°. For working features having a length after the bend, a bend angle of 15° has empirically been found to be the angle at which visibility of the tissue interaction site improves noticeably. Higher angles are of interest because they facilitate working in less flat regions, such as tissue recesses, where an ability to subtend a larger angle by simple rotation of the tool can be useful. A ratio of the diameter $D_1$ of the distal region to the diameter $D_2$ of the proximal region may be selected from a range of about 30% to about 60%. A length of the distal portion is selected from a range of 3-7 cm and a length of the proximal portion may be selected from a range of 11-35 cm. The proximal region may be electrically insulated for use, for example, with electrocautery or other electrosurgical technique. The proximal portion of the distal region may also be electrically insulated for use with electrosurgery such as electrocautery.

In another aspect, embodiments of the invention include a method for performing laparascopic surgery. The method includes providing a surgical tool including a longitudinal shaft having a distal region with an outer diameter $D_1$ less than an outer diameter $D_2$ of a proximal region of the shaft. A bend is defined in a portion of the distal region defining an offset $d_{off}$ between a distal tip of the shaft and a projection of a top surface of the proximal region, the top surface being a surface of the proximal region farthest from the distal tip. The bend may include a material with an elastic modulus, e.g., an elastic material. The distal region of the surgical tool may be inserted into a trocar having an inner diameter $D_3$ less than the offset $d_{off}$, and the tool advanced until the bend extends beyond a distal end of the trocar.

In yet another aspect, a method for designing a curved surgical tool for passing through a substantially straight trocar may include defining an inner diameter $D_3$ of a trocar through which the tool is to be inserted during use. Properties of the tool may be selected, such that the tool includes:
  a shaft having a distal region with a first diameter $D_1$ and a proximal region with a second diameter $D_2$, wherein $D_3 > D_2 > D_1$;
  a bend defined by a distal portion of the distal region, the bend defining an offset distance $d_{off}$ between a distal tip of the shaft and a top surface of the proximal region;
  a bend angle $\theta$;
  a bend radius R;
  a material with a predetermined elastic modulus; and
  length $L_{ab}$ of the distal region after the bend,
A maximum force required to advance the tool through the trocar (i) is based on an elastic modulus of the distal region of the tool and (ii) is less than a predetermined force.

One or more of the following features may be included. The tool may include an inner diameter $D_{id}$. The method may include selecting the length $L_{ab}$ prior to selecting the bend angle $\theta$, or selecting the bend angle $\theta$ prior to selecting the length $L_{ab}$. The method may include selecting the elastic modulus prior to selecting the bend angle $\Theta$. $(D_3 - D_2)/D_2$ may be less than 30%. $D_3 - D_2$ may be less than 2 mm.

BRIEF DESCRIPTION OF THE DRAWINGS

In what follows, preferred embodiments of the invention are explained in more detail with reference to the drawings, in which.

DETAILED DESCRIPTION OF THE PRESENTLY PREFERRED EMBODIMENTS

This invention may be accomplished by a surgical tool, and methods of using same for laparascopic surgery, including a longitudinal shaft having a distal region with an outer diameter $D_1$ less than an outer diameter $D_2$ of a proximal region of the shaft; and a bend defined in the distal region, the bend including an elastic material. In particular, the surgical tool is suitable for use during laparascopic surgery and capable of insertion through an access device during surgery. The tool includes a shaft having a longitudinal axis extending along at least a proximal region with diameter $D_2$, a distal region with a diameter $D_1$ and having an elastic modulus E, with diameter $D_2$ greater than diameter $D_1$. The distal region terminates in a working feature having a distal end. The shaft defines a bend in the distal region, the bend having a bend radius R, a bend angle $\Theta$, and a length after the bend $L_{ab}$. The distal region has a length L1 measured in a direction parallel to the shaft longitudinal axis, the distal region having an offset $d_{off}$ relative to the proximal region where $d_{off}$ is greater than $D_2$, and the bend angle $\Theta$ is greater than 10 degrees. The elastic modulus E and the length L1 are selected so that the working feature is insertable through the access device yet the distal region deflects less than 1 mm when a force of 10 N is applied perpendicular to the distal end of the working feature.

A method for performing laparascopic surgery includes inserting the distal region of the tool into a trocar having an inner diameter $D_3$ less than the offset $d_{off}$, and advancing the tool until the bend extends beyond a distal end of the trocar. A method for designing a curved surgical tool for passing through a substantially straight trocar includes defining an inner diameter $D_3$ of the trocar; and selecting properties of the tool, wherein a maximum force required to advance the tool through the trocar is based on an elastic modulus of the distal region of the tool and is less than a predetermined force.

A design of a surgical tool may be optimized to enhance its utility. For example, the positioning of the working feature at an angle with respect to the axis of the shaft may provide a number of clinical benefits, including potential increase in tissue access around contoured surfaces and ease of visualization. Tools with bends of roughly 15-45 degrees, and for regions after the bend of roughly 8 to 12 mm, may be preferable to improve visualization. In addition, a tool that can be inserted into a trocar with less than 10 N of force may also be preferable. It may be advantageous to have a tool that does not deflect noticeably under normal tissue probing, manipulation, and dissection.

Figure 1:
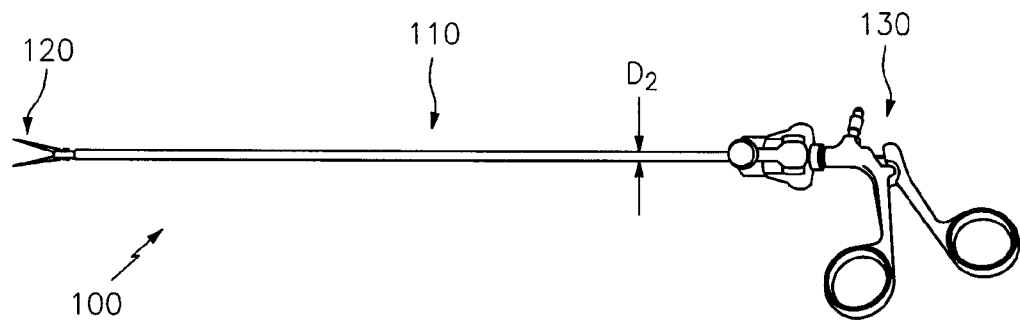
FIG. 1 is is a schematic side view of a conventional laparascopic instrument having movable jaws as a working feature.
Figure 2:
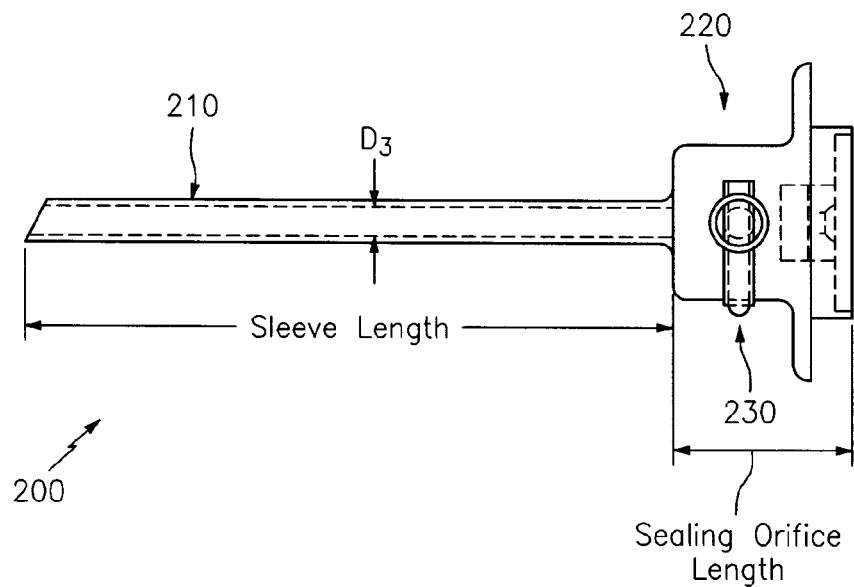
FIG. 2 is a schematic side view of a conventional trocar.
Figure 3A:
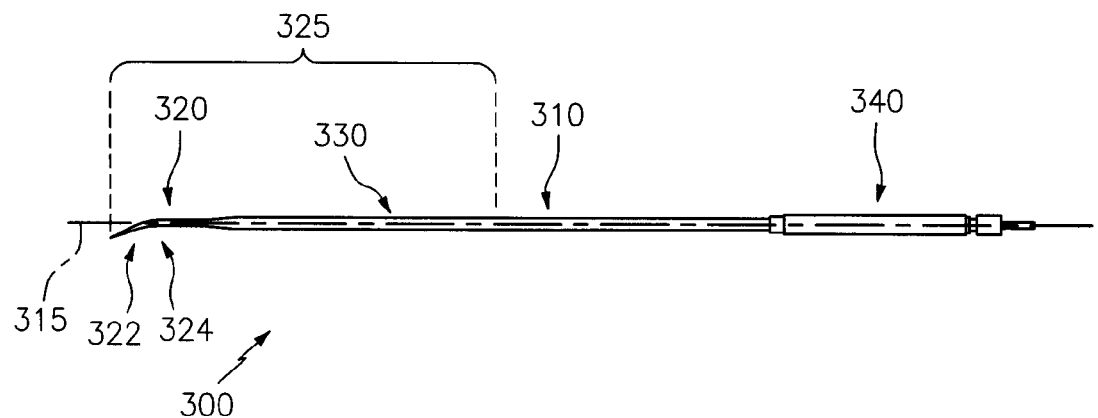
FIG. 3A is a schematic side view of a tool according to the present invention having a distal working feature with a bend relative to the longitudinal axis of the tool.

Referring to FIG. 3A, embodiments of the present invention include an elongated, substantially rigid, elastically deformable tool 300, suitable for insertion into a trocar sleeve of similar size, and for use in laparascopic surgery. The tool includes a longitudinal shaft 310 having a distal region 320 including a working feature 322, disposed at the distal end of a proximal region 330 of the shaft, with the working feature 322 having a bend 324 and an offset, described in more detail below. The tool as a whole has a main axis 315, which is defined by the longitudinal axis of the proximal region 330. In a number of constructions, the rigid shaft 310 extends proximally beyond the proximal region 330 to allow for attachment to a handgrip 340. The length inside the patient, extending beyond the distal end of the trocar sleeve 210, is defined as the length of an interior portion 325, FIGS. 3A and 3D. The proximal region 330 of the shaft 310 is preferably rigid, with no noticeable deflection under normal use. The tool preferably also includes a hand grip 340 proximal (away from the patient) to the proximal region, and depending on manufacturing design, attached to, or integral with the proximal region.

Figure 3B:
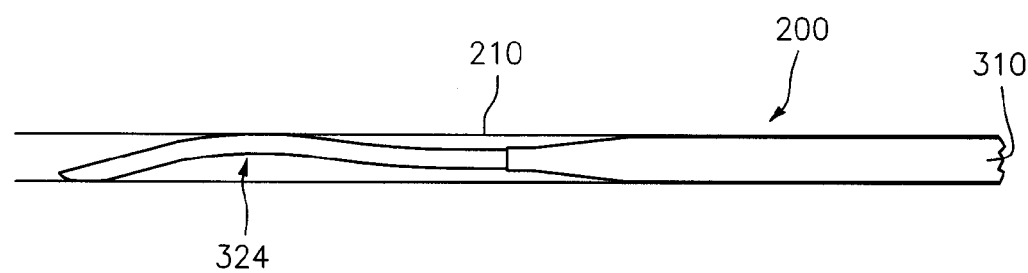
FIGS. 3B-3D are schematic side views of the tool of FIG. 3A at different stages of insertion relative to the trocar of FIG. 2.
Figure 3C:
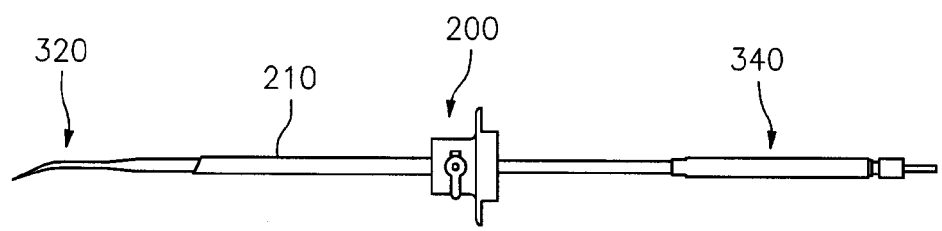

Referring to FIGS. 3B and 3C, in certain uses according to the present invention, the tool 300 is inserted into a trocar 200 having cannula or sleeve 210. During insertion, the distal region 320 typically straightens enough to pass through the sleeve 210 of the trocar, but retains a bend 324. For example, at least 30% of the bend may be retained during the advancement of the tool through the trocar. The proximal region may have a sliding fit with the trocar.

Figure 4A:
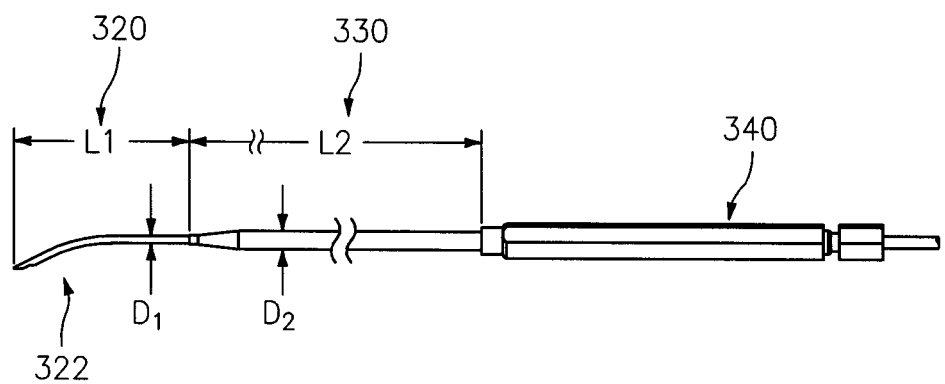
FIG. 4A is a schematic side view illustrating more details of the tool of FIG. 3A.

Referring to FIG. 4A, the proximal region 330 preferably has an outer diameter $D_2$ that is compatible with industry standard trocar sleeve sizes, e.g., with typical trocar sleeve sizes of 4 mm, 6 mm, or 9 mm. Examples of such trocars include Ethicon's ENDOPATH XCEL Trocar, model B5LT; Covidien's VERSAPORT V2 Trocar, model 179094; and Aesculap's Trocar, model EK014R. The working feature 322 is designed so that when used by surgeons, it does not deflect noticeably, that is, preferably has less than 1 mm of deflection.

As also illustrated in FIG. 4A, a maximum possible or total access length of the tool, measured along the main axis of the tool is L1+L2, in which L1 is a length of the working feature 322 (i.e., some or all of distal region 320) and L2 is a length of the proximal region 330. The appropriate total access length may be determined on the basis of a required access length between a tool insertion point within the patient and the furthest anatomical feature from that insertion point while the abdomen is under full insufflation pressure. While this varies from patient to patient, it is typical for a healthy adult patient to require an overall tool having an access length of L1+L2 of 29 cm to 33 cm, and an overall access length of 37 cm to 42 cm for use with obese patients. For pediatric patients, it can be as little as 14 cm to 26 cm. The overall length of the finished tool is determined by the size of the handle or grip, which typically ranges from 10 cm to 25 cm. The length of the sealing orifice is taken into account when selecting length L2.

The length L1 of the working feature (distal region), measured along an axis of the working feature, is preferably less than the length L2 of the proximal region of the shaft. The length L1 of the working feature may be less than the length of the trocar sleeve, in order to protect the junction of L1 and L2 during tool insertion and retraction through the trocar, as it could inadvertently be damaged by exerting torque on the device, i.e. exerting a force which is not substantially parallel to the axis of the trocar. Using a typical trocar sleeve length of 10-12 cm results in a preferable L1 range of 3-7 cm, with a corresponding L2 of 11-35 cm.

The O.D. $D_1$ of the working feature (distal region) is less than the O.D. $D_2$ of the rigid shaft (proximal region). A ratio of the diameter $D_1$ to $D_2$ may be selected from a range of about 30% to about 60%. This O.D. ratio reduces the amount of tool material visible within the surgical field, aiding surgeon visualization, and provides straightforward design and manufacturing options for making the working feature more flexible than the proximal part of the tool to which it is attached.

Figure 4B:
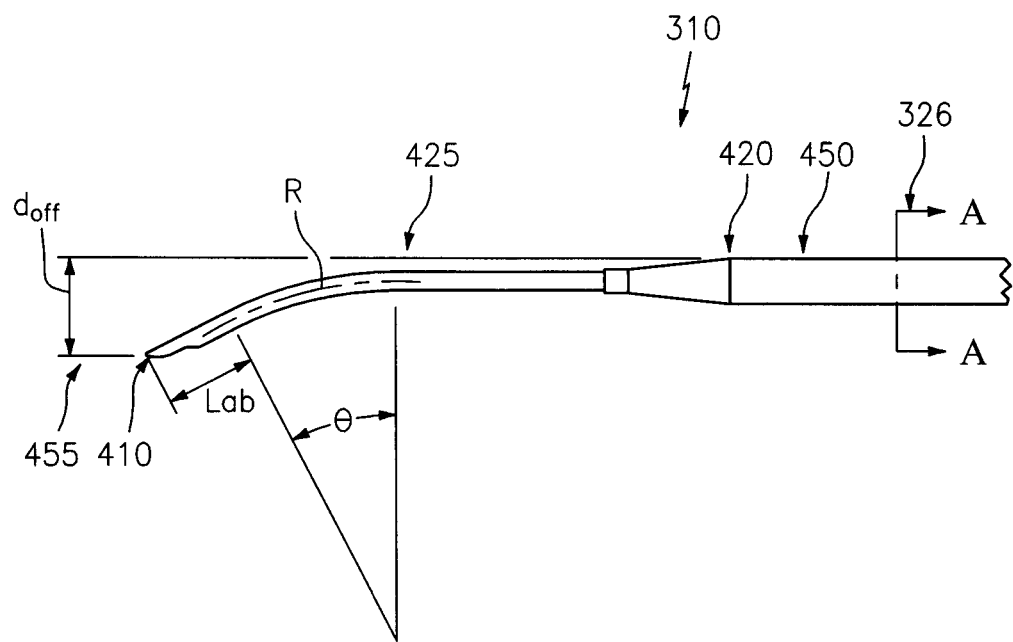
FIG. 4B is an enlarged schematic side view of the working feature of a tool according to the present invention.

Referring to FIG. 4B, the working feature (i.e., some or all of distal region 320) has a predefined bend, with a radius R and angle Θ. A length $L_{ab}$ of material is disposed after the bend. The bend may include a material having an elastic modulus, e.g., an elastic material, such as a metal, e.g., stainless steel 304SS, with an elastic modulus of 195 GPa, or a glass, such as Corning Willow glass, with an elastic modulus of 70-80 GPa. The material is selected so that the yield strength preferably precludes plastic deformation while passing the tool into and out of the trocar.

Figure 3D:
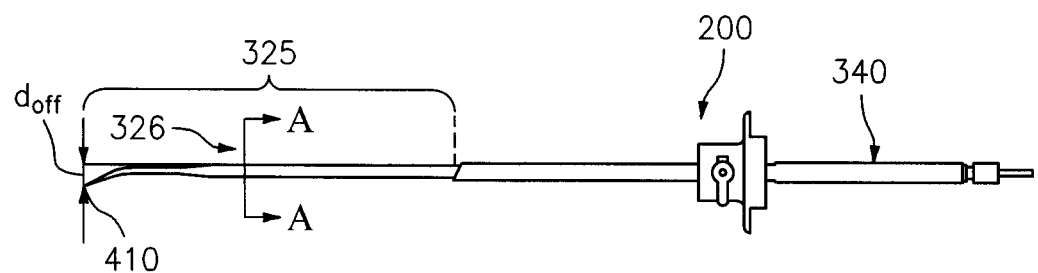
Figure 4C:
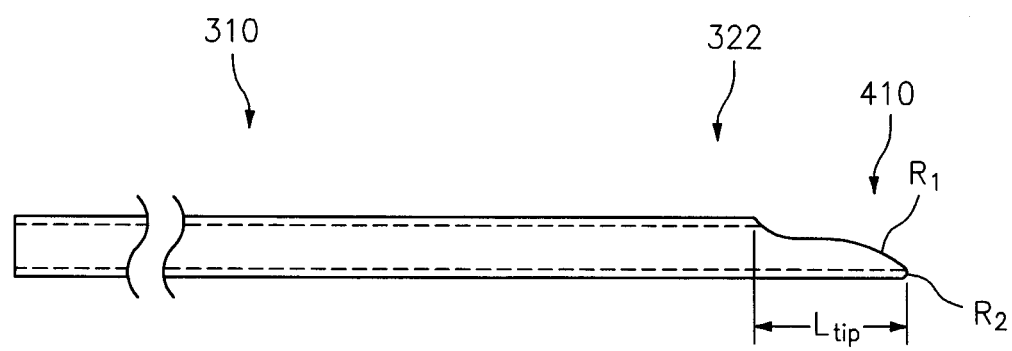
FIG. 4C is an enlarged schematic side view of the tip of the working feature of the tool of FIG. 4B prior to imparting a bend.

An offset $d_{off}$ may be defined as the length of the projection of the interior portion of the tool 325 in a plane that is parallel to the radial cross section 326, indicated in FIGS. 3D and 4B as a cross-sectional view along lines A-A, of the proximal region 330. Moreover, the offset may also be described using geometric parameters:

$$d_{off}=(1-\cos \theta)*R+(\sin \theta)*L_{ab}+D_1/2+D_2/2 \quad \text{EQ. 1:}$$

or, for the case of a recessed tip, as illustrated in FIG. 4C:

$$d_{off}=(1-\cos \theta)*R+(\sin \theta)*L_{ab}+D_2/2. \quad \text{EQ. 2:}$$

Referring still to FIG. 4B, offset $d_{off}$ may be a distance between the distal tip 410 of the shaft and an extension of an upper or top surface 450 of the proximal region 330, being indicated by line 425 extending from point 420, at which the shaft begins a transition to a narrower diameter for the distal region. The top surface 450 is an uppermost longitudinal surface of the proximal region farthest from the distal tip, that is, the greatest distance from the distal end in a direction normal to the longitudinal axis. For example, if the proximal region is circular or oval, the top surface may be a line disposed along the longitudinal surface farthest from the distal tip and parallel to the main axis 315, FIG. 3A, extending through the longitudinal shaft 310. Similarly, if the proximal region has flat surfaces, the top surface is the longitudinal surface farthest from the distal tip and parallel to the main axis of the longitudinal shaft. The extension, as shown by line 425, FIG. 4B, extends from the top surface to beyond the distal tip 410. The offset distance $d_{off}$ may be measured perpendicularly between a first and a second parallel line 425, 455, the first line extending from the top surface of the proximal region and the second line including the distal tip 410 of the shaft 310.

Referring to FIG. 4C, the distal-most portion of the shaft may be shaped on the inside of the bend, thereby recessing the tip with respect to the trocar, and creating a final shape that is more shovel, or spoon shaped. Radii of curvature $R_1$ and $R_2$ define the shape of the tip. This may be desirable for tissue manipulation by working feature 322, and may also distribute force on the inside of the trocar while the working feature 322 is passed through the trocar sleeve as shown in FIG. 3B. Design consideration may be given for $R_1$, $R_2$, and tip length $L_{tip}$, which determine the surface area of the tool tip that contacts the trocar sleeve during tool insertion and retraction. For the case of a recessed tip, the offset $d_{off}=(1-\cos \theta)*R+(\sin \theta)*L_{ab}+D_2/2$.

Figure 4D:
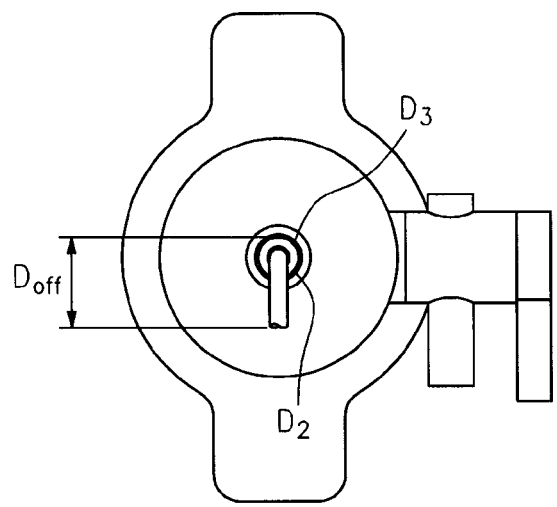
FIG. 4D is a front view of the tool of the tool disposed in the trocar of FIGS. 3C and 3D.

Referring to FIG. 4D, this design allows an overall working feature offset $d_{off}$ that is preferably larger than the rigid shaft (proximal region) O.D. $D_2$ and preferably larger than the trocar sleeve I.D. $D_3$. A ratio of (a difference in an inner diameter $D_3$ of the trocar and the outer diameter $D_2$ of the proximal region)/$D_2$ may be selected from a range of 10% to 30% to allow for proper insufflation sealing.

One or both of the distal and proximal regions may define one or more lumens. In particular, the working feature (distal region) may have a hollow channel, allowing insertion of an optical waveguide or other flexible energy device, or may not have a hollow channel, instead being used as a contact for electrocautery or blunt tissue manipulation. Additional hollow channels may be used for complementary features, such as saline irrigation, or used with multi-element electrocautery.

The distal region may be designed for use as an electrocautery device. The proximal, and some section of the distal if needed, regions may be insulated electrically be a non-conductive polymer coating. The coating is preferably biocompatible, and has a sufficiently low Young's modulus to not significantly affect the mechanical properties of the distal region of the tool. An exemplary suitable material is Polyethereketone PEEK, High Density Polyethelene "HDPE", or Acrylonitrile butadiene styrene "ABS". The material may be applied by of insert molding, over-molding, or by attaching a separately extruded sheath. The distal and proximal regions materials may provide sufficient electrical conduction, or internal wires of sufficient electrical conduction may be run through working channels of the device. Exemplary materials for electrical conduction are stainless steel, silver, and brass. The proximal portion of the method for electrical conduction may terminate in terminal posts typically used for attachment to electrosurgical generators.

Figure 5A:
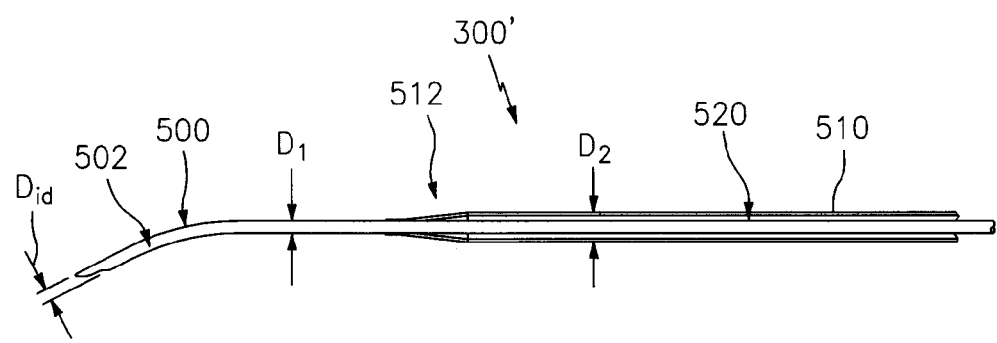
FIGS. 5A-5B are side cross-sectional views of tools fabricated in accordance with embodiments of the invention.

Referring to FIG. 5A, in one embodiment of the invention, a tool 300' is a "two component" embodiment, having a thin wall smaller OD tube 500 with a lumen 502 extending along the length of the tool 300', and extending inside a rigid larger OD shaft 510, which itself has a lumen 520, into which the thin-wall, smaller OD tube 500 is inserted. The rigid shaft may be tapered at transition region 512 prior to, or during, attachment to the thin wall smaller OD tube 500 via brazing, welding, or epoxy. The rigid shaft 510 is preferably shorter than the thin wall tube 500 which protrudes from it. The tool also includes a hand grip that may be attached to the rigid shaft via a knurled press fit (not shown). The hand grip may also be attached via press fit, adhesive, brazing, or welding to the rigid shaft. This may create a light weight tool, weighing 0.07 lb in one construction using 304 Stainless Steel "304SS" material and an Al 6061 hand grip, that is suitable for a range of cleaning and sterilization approaches. This manufacturing approach also allows use of differing materials for the working feature and proximal region, allowing varying materials with varying elastic moduli to be used. A non-conductive material may be used for the rigid larger OD shaft, creating an insulation barrier necessary for use as an electrocautery device.

Figure 5B:
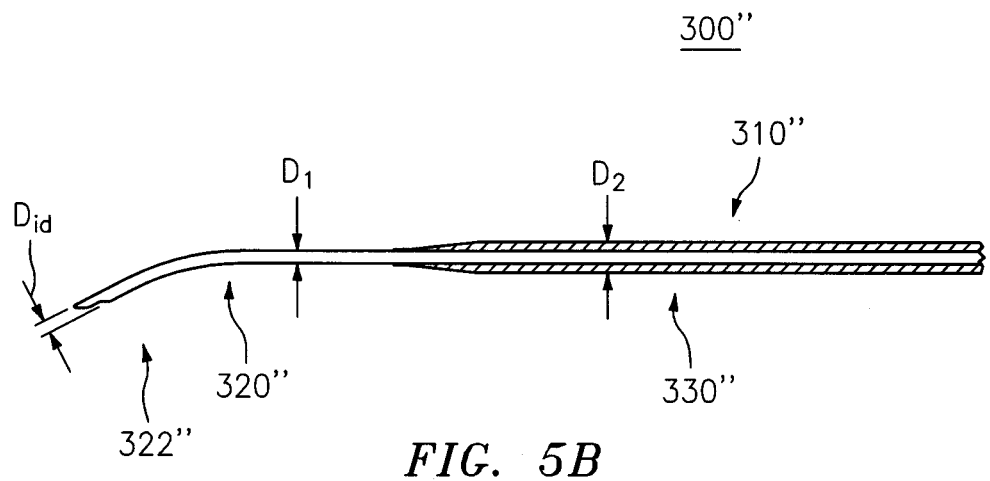

Referring to FIG. 5B, another embodiment of the invention includes machining or otherwise removing material from a single, monolithic shaft 310" with intended final I.D. and O.D. equal to that of the rigid proximal region 330". The distal region 320" of the shaft 310" is machined to define a working feature by being turned down to the intended smaller O.D. of the working feature region 322" using a lathe or Swiss turning machine, for example. The single-piece construction tool 300" can then be attached to the hand grip (not shown) via a press fit, adhesive, or welding process. This construction creates a heavier tool that may reduce hand-induced vibration and increase overall tool robustness. As an example, replacing use of a 1.6 mm I.D., 2.1 mm O.D. lumen with 4.0 mm I.D., 5.0 mm O.D. rigid shaft of 304SS material with a single shaft of 1.6 mm I.D., 5.0 mm O.D. 304SS would increase the overall tool weight by a factor of 28, from 0.07 lb to 2.0 lb.

Embodiments of tools described herein may be used to perform laparoscopic surgery. For example, the distal region of a tool may be inserted into a trocar having an inner diameter $D_3$ less than the offset $d_{off}$. The tool may be advanced until the bend extends beyond a distal end of the trocar. The force that needs to be applied to advance the tool may be less than about 10 N. The bend may be substantially retained during the advancement of the tool through the trocar, for example at least 30% of the bend may be retained during advancement of the tool. A waveguide may be passed through a lumen in the shaft. Alternatively, electrocautery or tissue manipulation may be performed with the tool.

In one model that can be utilized to select design criteria for tools made and utilized according to the present invention, it may be advantageous for a surgeon to exert no more than 10 N (Newtons) of force when inserting a tool through a trocar sleeve, and it can be desirable to have a tool with a bend angle, R, and $L_{ab}$ of sufficient size to aid working feature access and visualization. Thus, it is useful to have an analytical model to explore design possibilities, to thereby define tool dimensions that meet the needs of surgeons.

Friction force is a function of the normal force imparted by the surgical tool onto the walls of the trocar, and the coefficient of friction between the two objects. The normal force of each contact point of the working feature within the trocar sleeve can be modeled using the simplified Euler-Bernoulli beam theory:

$$q(x) = \frac{EI d^4 w}{dx^4} \qquad \text{EQ. 3}$$

where q(x)=distributed load, w(x)=deflection, E=elastic modulus, and I=second moment of area. The second moment of area can be represented as:

$$I = \frac{\pi}{64}(D_1^4 - D_{id}^4) \qquad \text{EQ. 4}$$

$D_1$=Working feature outer diameter; and
$D_{id}$=Working feature inner diameter (note, in the case of a solid feature, the inner diameter=0).

For the results below, it is assumed that the rigid part of the tool with diameter $D_2$ is coaxial (fixed and centered) with respect to $D_3$, a reasonable assumption given that there is only a small amount of play between the tool and the trocar.

The friction force may be calculated in several steps:
1. Start with the shape of the un-deformed (outside the trocar) tool y(x), where x is the coordinate parallel to the trocar axis, and y is other coordinate in the plane of the tool bend.
2. The Euler-Bernoulli beam equations are applied at three locations along the tool:
   a. The point where the working feature is connected to the rigid shaft (x=0). At this location, the deflection w(x=0) and the slope of the deflection $$\left.\frac{dw}{dx}\right|_{x=0}$$

must both be zero.
   b. The tip of the working feature (x=L1). At this location, the tip is in contact with the sleeve, and the bending moment is 0.

c. The intermediate point (x=l, with 0<l<L1) where the working feature touches the sleeve on the opposite side. At this location, the working feature touches tangentially the sleeve, the slope is zero, and the momentum is equal on both sides of the contact point.
3. The deflection w(x) is described by $3^{rd}$ order polynomials in each free section, between 0 and l, and between l and L1. For 0<x<l, $w(x)=a_1+a_2x+a_3x^2+a_4x^3$. Similarly for l<x<L1, $w(x)=a_5+a_6x+a_7x^2+a_8x^3$
4. The boundary conditions described in item 2 above result in the following system of equations:

$$Ma = b, \text{ where } M \text{ and } b \text{ are defined as} \quad \text{EQ. 5}$$

$$M = \begin{pmatrix} 1 & 0 & 0 & 0 & 0 & 0 & 0 & 0 \\ 0 & 1 & 0 & 0 & 0 & 0 & 0 & 0 \\ 1 & l & l^2 & l^3 & 0 & 0 & 0 & 0 \\ 0 & 1 & 2l & 3l^2 & 0 & 0 & 0 & 0 \\ 0 & 0 & 0 & 0 & 1 & l & l^2 & l^3 \\ 0 & 0 & 0 & 0 & 0 & 1 & 2l & 3l^2 \\ 0 & 0 & 0 & 0 & 1 & L1 & L1^2 & L1^3 \\ 0 & 0 & 0 & 0 & 0 & 0 & 2 & 6L1 \end{pmatrix}$$

$$b = \begin{pmatrix} 0 \\ 0 \\ -\delta - y(x=l) \\ -\frac{dy}{dx}(x=l) \\ -\delta - y(x=l) \\ -\frac{dy}{dx}(x=l) \\ \delta - y(x=L1) \\ 0 \end{pmatrix}$$

$$\text{and } \delta = \frac{D_B - D_1}{2}$$

In addition, the conserved moment at x=l requires that $2a_7+6a_8l=2a_3+6a_4l$

Solving for $a_1$ through $a_8$ and then calculate the friction force as $F=6*\mu*E*I*(|a_4|+|a_8-a_4|+|a_8|)$, where μ is the friction coefficient between the working feature and the sleeve.    EQ. 6:

The model also requires a coefficient of friction between the two materials of interest. In this case, for the chosen pair of materials for the tool and trocar, the coefficient of friction was determined experimentally to be to be 0.07. The materials used were the 304SS of the tool shaft inside Ethicon's ENDOPATH XCEL Trocar. Different pair of materials have different coefficients of friction, which provides another materials-related engineering parameter that can be selected to permit and expand the range of permitted geometries. For example, a pair of materials having a lower coefficient of friction may result in lower friction forces, and thus, less force needed to insert the tool through the trocar. One such pair is stainless steel and polytetrafluoroethylene "PTFE", considered to have a coefficient of friction of 0.04. This is one way, the range of permitted angles Θ and lengths after the bend $L_{ab}$ can be increased further.

Figure 6:
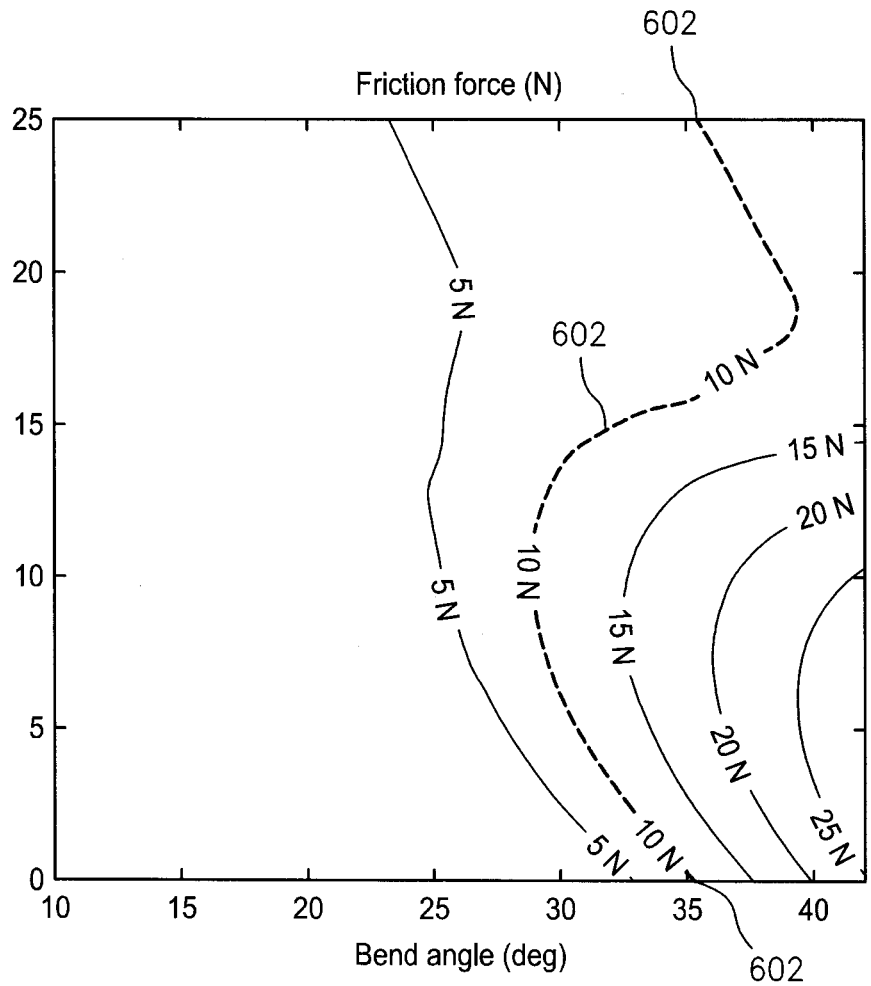
FIG. 6 is a graph showing isoforce lines for combinations of bend angle $\Theta$ and length after the bend $L_{ab}$ for the conditions in table 1, and for a 6 mm trocar.

Applying the above model, it can be determined that the following tool attributes can be altered to affect the normal force applied to the trocar sleeve:

Bend radius R, angle Θ, total working feature length L1, working feature length after the bend Lab, and inner diameter of the trocar sleeve $D_3$. These attributes determine the deflection w(x).
Elastic modulus of the working feature material E
Working feature inner diameter $D_{id}$
Working feature outer diameter, $D_1$ Referring to FIG. 6, friction force has been plotted versus length after the bend $L_{ab}$ and bend angle Θ, for a trocar sleeve 6 mm in inner diameter, keeping the other design criteria fixed as below in Table 1. The lines in FIG. 6 are lines of constant force, or "isoforce" lines in Lab and Θ space. The thick dotted line 602 is the maximum acceptable isoforce line for 10 N of insertion force. The area to the left of the thick dotted line shows design parameters that result in a requirement of less than 10 N of force to insert the tool through a trocar sleeve 6 mm in diameter.

TABLE I

Table 1. Fixed Design Parameters used in simulations in FIG. 6, 7, 8 and 9.

$D_{id}$ = 0.063"
$D_1$ = 0.083"
R = 40 mm
L1 = 2.0"
E = 193 Gpa
$D_2$ = 0.197" (5 mm)
Coefficient of Friction = 0.07

In other words, fixed parameters of the device are: Inner diameter=0.063", Outer diameter=0.083", Bend radius=40 mm, Total length=2.0", Elastic modulus=193 GPa. FIG. 6 shows the surprisingly large range of angles and offsets that are possible for use with a 6 mm trocar sleeve, and a requirement that the surgeon need exert no more than 10 N to insert the tool through the trocar sleeve.

TABLE 2

Table 2 illustrates exemplary designs of length after the bend: Lab and bend angle: Θ

| | Lab (mm) | | | | | | |
|---|---|---|---|---|---|---|---|
| | 2 | 4 | 8 | 10 | 12 | 16 | 20 |
| Maximum bend angle for Friction Force , 10 N in degrees | 34 | 31 | 29 | 29 | 29 | 36 | 39 |

A bend angle θ of 27 degrees and $L_{ab}$ of 10 mm may be preferred by surgeons, which is readily achievable. This results in an offset $d_{off}$ of approximately 2. Referring to FIG. 4D, this means that the distal end of the working feature, when viewed facing the shaft, appears twice as wide as the shaft. In some embodiments, a bend angle may be selected from a range of 15 degrees to 45 degrees. While the supplied figures do not span the full range of angles and Lab, altering other tool variables will allow acceptable friction forces for all proposed ranges. For example, selecting a different pair of materials may lower the coefficient of friction, thus expanding the design parameter space. Simulations have been run showing the surprising range of offsets possible using different starting assumptions.

Figure 7:
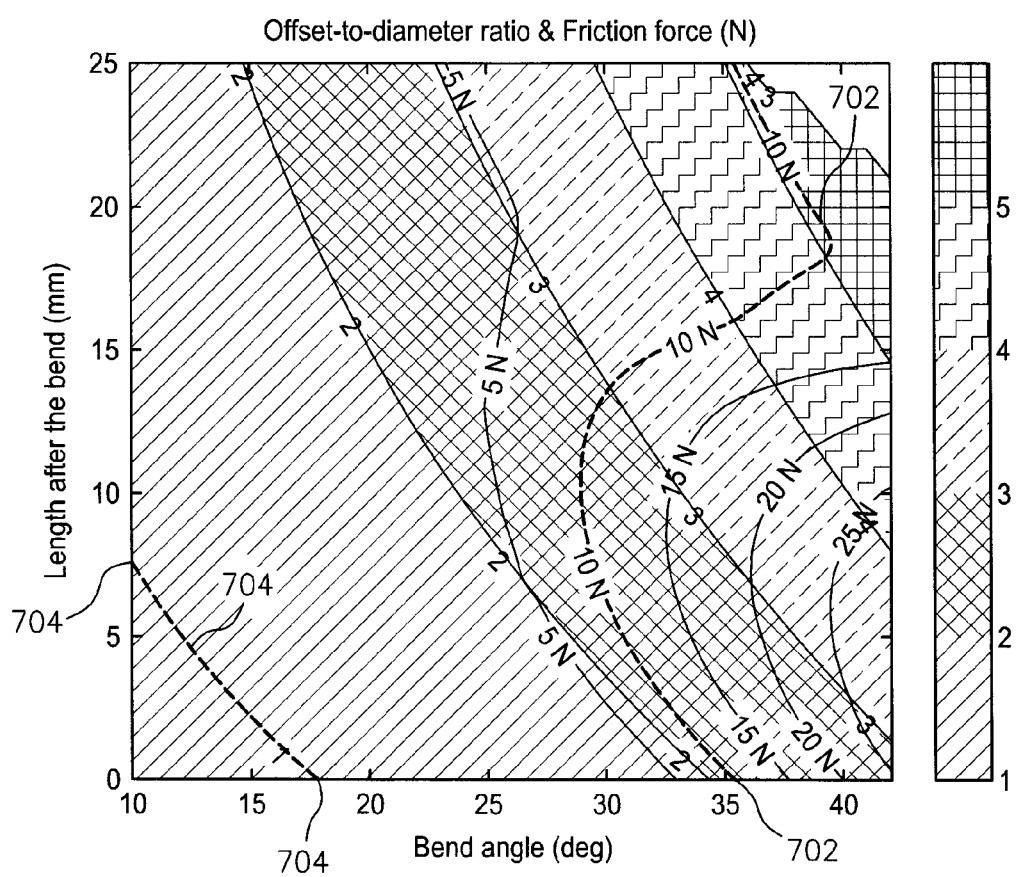
FIGS. 7-10 are each a composite of two overlaid maps, one of isoforce lines, the second of iso-offset lines, which together illustrate acceptable combinations of bend angle $\Theta$ and length after the bend $L_{ab}$ for a given offset and a given insertion force.

FIG. 7 shows the lines of "same offsets" $d_{off}$, or iso-offset, for the starting assumptions of the above example. A contour plot of offset-to-diameter ratio $d_{off}/D2$ is shown in gray shades. A $d_{off}/D_2$ ratio of 1.0 is shown as a thick dashed line

704. For parameters to the right of this line, the $d_{off}/D_2$ ratio is larger than 1.0 and reaches all the way to 5.0. Overlaid on this is a contour plot of the friction force (with labels denoting friction force in newtons N). The acceptable friction force threshold is shown as a thick dotted line 702. As seen, offsets between 2 and 2.5, and bend angles between 25 and 30 degrees are easily achieved for lengths after the bend of 8-12 mm. These are clinically interesting, as they generate a bend configuration that significantly increases access around contoured anatomical surfaces in comparison to tools that do not have similar working feature attributes. Fixed parameters of the device are: Inner diameter=0.063", Outer diameter=0.083", Bend radius=40 mm, Total length=2.0", Elastic modulus=193 GPa. Trocar sleeve ID is 6.0 mm.

Figure 8:
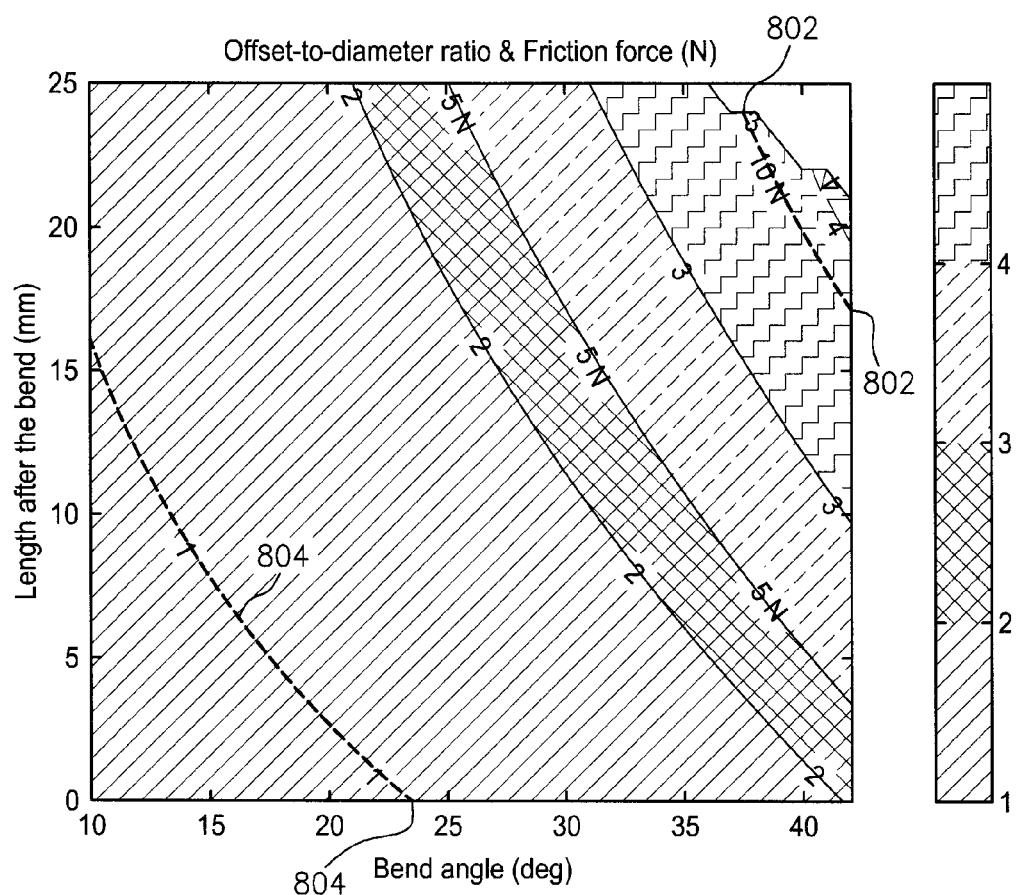

This "offset" analysis can also be applied to trocars with larger ID sleeves. See FIG. 8 which shows lines of iso-offset for a 9 mm trocar sleeve ID, otherwise starting with all the assumptions in Table 1. Not surprisingly, the working feature design space is larger when the opening of the trocar sleeve is larger. For a trocar sleeve having a 9 mm ID, staying with all the assumptions present in Table 1, $d_{off}/D_2$ ratios up to 3.7 can be achieved while keeping friction force below 10 N. FIG. 8 is a contour plot of offset-to-diameter ratio $d_{off}/D_2$ (gray shades). $d_{off}/D_2$ ratio of 1.0 is shown as a thick dashed line 804. For parameters to the right of this line, the $d_{off}/D_2$ ratio is larger than 1.0 and reaches all the way to 5.0. Overlaid on this is a contour plot of the friction force (with labels denoting friction force in newtons). The acceptable friction force threshold is shown as a thick dotted line 802. Fixed parameters are: Inner diameter=0.063", Outer diameter=0.083", Bend radius=40 mm, Total length=2.0", Elastic modulus=193 GPa.

This analysis can also be applied to trocars with smaller ID trocar sleeves. See FIG. 9 which shows lines of isooffset for a 4 mm trocar sleeve ID, otherwise starting with all the assumptions in Table 1. The design space is clearly smaller overall, the range of values to the left of the thick dotted line, yet an offset ratio, $d_{off}/D_2$ greater than one can easily be achieved.

Contour plot of offset-to-diameter ratio $d_{off}/D2$ (gray shades). $d_{off}/D_2$ ratio of 1.0 is shown as a thick dashed line 904. For parameters to the right of this line, the $d_{off}/D2$ ratio is larger than 1.0 and reaches all the way to 5.0. Overlaid on this is a contour plot of the friction force (with labels denoting friction force in newtons). The acceptable friction force threshold is shown as a thick dotted line 902. Fixed parameters are: Inner diameter=0.063", Outer diameter=0.083", Bend radius=40 mm, Total length=2.0", Elastic modulus=193 GPa.

Figure 9:
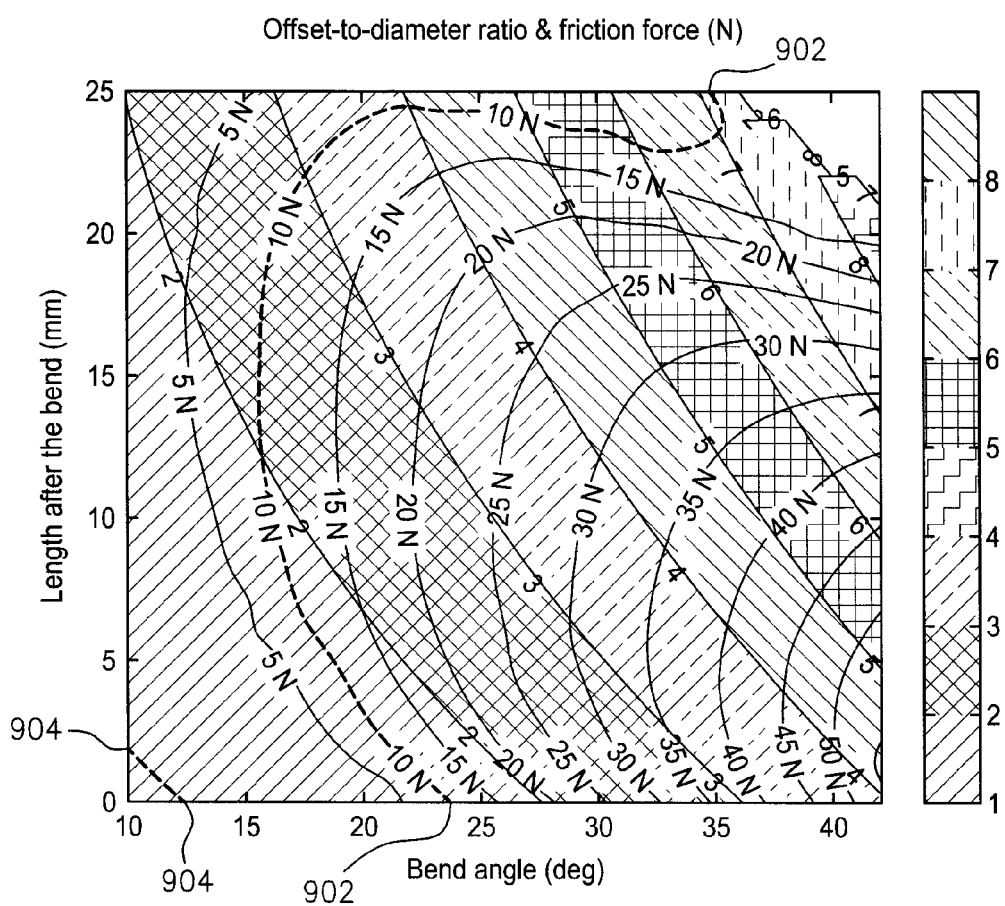

To expand the acceptable parameter window in FIG. 9, the friction force can be reduced by designing a tool with a thinner wall, which will make it more flexible, while maintaining the necessary rigidity with respect to tissue upon exit from the trocar sleeve.

Figure 10:
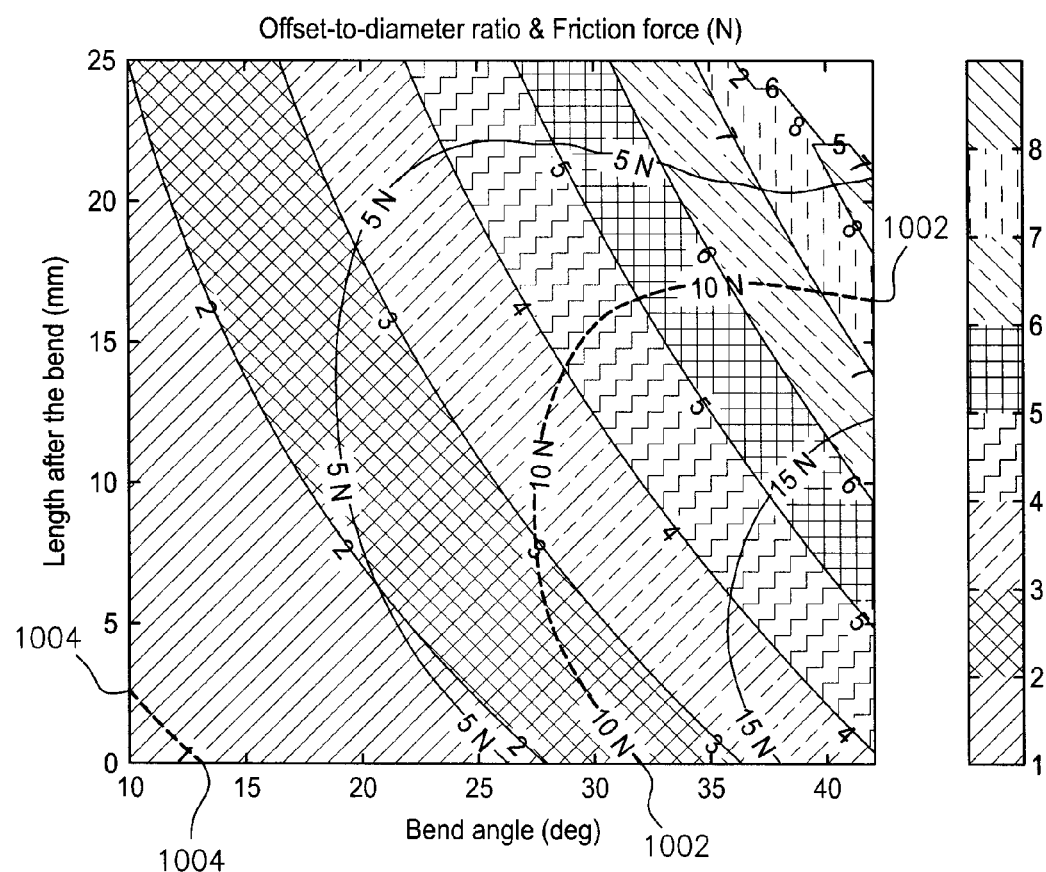

Referring to FIG. 10, results are shown for an outer diameter of 0.073" (half the wall thickness). The acceptable parameter window is now much wider, and friction force can be kept below 10 N, while achieving offset-to-diameter ratios in excess of 3 or more.

Table 3 shows the set of fixed parameters used for the simulation in FIG. 10:

TABLE 3

Fixed Design Parameters used in simulations in FIG. 10

$D_{id}$ = 0.063"
$D_1$ = 0.073"
R = 40 mm

TABLE 3-continued

Fixed Design Parameters used in simulations in FIG. 10

L1 = 2.0"
E = 193 Gpa
$D_2$ = 0.197" (5 mm)
Coefficient of Friction = 0.07

In other words for FIG. 10, a contour plot of offset-to-diameter ratio $d_{off}/D2$ is indicated by gray shades. A $d_{off}/D2$ ratio of 1.0 is shown as a thick dashed line 1004. For parameters to the right of this line, the $d_{off}/D2$ ratio is larger than 1.0 and reaches all the way to 5.0. Overlaid on this is a contour plot of the friction force (with labels denoting friction force in newtons). The acceptable 10 N friction force threshold is shown as a thick dotted line 1002. Fixed parameters are: Inner diameter=0.063", Outer diameter=0.073", Bend radius=40 mm, Total length=2.0", Elastic modulus=193 GPa.

A curved surgical tool for passing through a substantially straight trocar may be designed as follows. An inner diameter $D_3$ of a trocar through which the tool is to be inserted during use may be defined. Then, the properties of the tool may be selected, so that the tool includes:

a shaft having a distal region with a first diameter $D_1$ and a proximal region with a second diameter $D_2$, wherein $D_3 > D_2 > D_1$;

a bend defined by a distal portion of the distal region, the bend defining an offset distance $d_{off}$ between a distal tip of the shaft and a top surface of the proximal region;

a bend angle θ;

a bend radius R;

a material with a predetermined elastic modulus; and length $L_{ab}$ of the distal region after the bend, such that a maximum force required to advance the tool through the trocar (i) is based on an elastic modulus of the distal region of the tool and (ii) is less than a predetermined force. The tool may include inner diameter $D_{id}$. The length $L_{ab}$ may be selected prior to selecting the bend angle θ. Alternatively, the bend angle θ may be selected prior to selecting the length $L_{ab}$. The elastic modulus may be selected prior to selecting the bend angle Θ. The relationship between $D_2$ and $D_3$ may be: $(D_3-D_2)/D_2 < 30\%$. In some embodiments, $D_3 - D_2 < 2$ mm.

In one Example, Tools 1 and 2 were made using the design criteria described below. The two dimensions of the two tools were identical in every way except the length of the working feature. The material used, 304SS, was also the same.

TABLE 4

Table 4: A comparison of two tools one with a working feature 2.5 times longer than the other.

|  | Tool 1 | Tool 2 |
| --- | --- | --- |
| $D_3$ | 6 mm | 6 mm |
| $D_1$ | 2.1 mm | 2.1 mm |
| $D_{1id}$ | 1.6 mm | 1.6 mm |
| L1 | 5 cm | 12.5 cm |
| $D_2$ | 5 mm | 5 mm |
| L2 | 27.7 cm | 27.7 cm |
| R | 4 cm | 4 cm |
| Θ | 27 deg | 27 deg |
| Lab | 10 mm | 10 mm |
| $d_{off}$ (calculated) | 11.4 | 11.4 |
| $d_{off}$ (measured) | (average of 3 tools) 9.96 mm | 10.01 mm |

TABLE 4-continued

Table 4: A comparison of two tools one with a working feature 2.5 times longer than the other.

|  | Tool 1 | Tool 2 |
|---|---|---|
| End of tip cutout | Yes | Yes |
| $d_{off}/D_2$ (measured) | 1.99 | 2.01 |
| $d_{off}/D_3$ (6 mm) | 1.66 | 1.68 |
| Material | 304SS | 304SS |
| E | 193 GPa | 193 GPa |
| Deflection seen while performing a procedure (noted not measured) | acceptable | unacceptable |
| Force to push tool through trocar having $D_3$ of 6 mm (measured) | 7 N | 6 N |
| Deflection as calculated under 10 N | 8 mm | 0.5 mm |
| Rigidity (calculated) | 19 exp 3 N/m | 1.3 exp 3 N/m |

Note, both of these tools has shaved tips, per the illustration in FIG. 4D.

Both tools easily met the "less than 10 N" requirement, but the first one, which could be pushed through the trocar with a force of 6 N was too soft to be considered useful for probing, manipulating and dissecting tissue.

The rigidity of the tool is described by this equation:

$$\frac{E(D_1^4 - D_{ID}^4)}{L1^3} = \text{Rigidity in N/m} \quad \text{EQ. 7}$$

Where E=the elastic modulus of the material, L1=the length of the "beam" being deflected, which in this case is the length of the working feature, $D_1$=the outer diameter of the working feature, and $D_{ID}$ is the inner diameter of the working feature.

Thus, it is readily modified, thereby addressing the practical concerns of surgeons, by the simple approach of shortening the L1, as rigidity is inversely proportional to the cube of the length. As seen in Table 4 above, reducing the length of the working feature from 12.5 cm to 5 cm increases the calculated rigidity by over a factor of 10, from $1.3 \times 10^3$ N/m, to $19 \times 10^3$ N/m, and produced a tool that surgeons liked. Selecting a stiffer material would also work, and using a working feature with thicker walls would work a well. Thus, rigidity of the working feature at the tissue interface may easily be brought into a clinically useful range, while the other desirable attributes are easily maintained.

Tool 2 has been used successfully in a number of laparascopic procedures, including but not limited to adhesiolysis, endometrial ablation, and ovarian cyst removal. Endometrial ablation is well suited in particular due to the typical nature of the disease, in which uterine cells begin to implant and grow outside the uterus. These cells are typically found in areas of the abdomen that are difficult to access by traditional laparascopic tooling, and which a larger working feature offset is preferable.

Although specific features of the present invention are shown in some drawings and not in others, this is for convenience only, as each feature may be combined with any or all of the other features in accordance with the invention. While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. A method for performing laparascopic surgery in a patient through an access device, comprising:
    selecting an access device having an inner wall cross-sectional perimeter $P_3$;
    inserting the access device into the patient to provide laparascopic access;
    selecting a surgical waveguide conduit tool including a shaft including a rigid proximal region having a length L2 along a proximal region longitudinal axis, the rigid proximal region including a proximal lumen, and having a cross-sectional perimeter $P_2$ that is perpendicular to the proximal region longitudinal axis, and a distal region coupled to the proximal region and having a length L1 measured in a direction parallel to the proximal region longitudinal axis, the distal region including a distal lumen communicatively coupled to the proximal lumen, the distal region having a cross-sectional perimeter $P_1$ that is perpendicular to the proximal region longitudinal axis, $P_1$ being less than $P_2$, the distal region including an integral working feature and having a bend located between the working feature and the proximal region, the working feature having a rounded distal tip and an opening that has an opening perimeter that is greater than the cross-sectional perimeter $P_1$ of the distal region, the opening defines an S-shaped curve including a first curve having a first orientation of curvature and a second curve having a second orientation of curvature that is opposite to the first orientation of curvature;
    inserting the waveguide conduit tool directly into the access device, after the access device has been inserted into the patient, using less than 10 N of force;
    inserting an optical waveguide through the proximal lumen and the distal lumen; and
    utilizing the waveguide conduit tool to deliver optical energy through the optical waveguide.

2. The method of claim 1 wherein the access device includes a trocar having an inner diameter $D_3$, the rigid proximal region has an outer diameter $D_2$, the distal region has an outer diameter $D_1$ that is less than $D_2$, and the opening perimeter is greater than an outer circumference of the distal region.

3. The method of claim 2 wherein the distal region of the selected surgical waveguide conduit tool has an elastic modulus E within a range from 193 GPa inclusive to 195 GPa inclusive, the bend has a bend angle $\Theta$ that is greater than 10 degrees in a resting state, the distal region has an offset $d_{off}$ relative to the proximal region, and $d_{off}$ is greater than both $D_2$ and $D_3$.

4. The method of claim 3 wherein offset $d_{off}$ is at least 1.5 times as large as diameter $D_3$ and at least the distal region of the shaft is formed of a stainless steel material.

5. A method for making a surgical waveguide conduit tool comprising:

selecting a trocar having an inner diameter $D_3$; and forming the surgical waveguide conduit tool to have a shaft including a rigid proximal region having a length $L2$ along a proximal region longitudinal axis, the rigid proximal region including a proximal lumen, and having an outer diameter $D_2$, and a distal region coupled to the proximal region and having a length $L1$ measured in a direction parallel to the proximal region longitudinal axis, the distal region including a distal lumen communicatively coupled to the proximal lumen and having an outer diameter $D_1$ that is less than $D_2$, the distal region including an integral working feature and having a bend located between the working feature and the proximal region, the working feature having a rounded distal tip and an opening that has a perimeter that is greater than a circumference of the distal region, the opening defines an S-shaped curve including a first curve having a first orientation of curvature and a second curve having a second orientation of curvature that is opposite to the first orientation of curvature, wherein the bend has a bend angle $\Theta$ that is greater than 10 degrees in a resting state, the distal region has an offset $d_{off}$ relative to the proximal region, and $d_{off}$ is greater than both $D_2$ and $D_3$.

6. The method of claim 5 wherein offset $d_{off}$ is greater than $(1.5)(D_2)$ and at least the distal region of the shaft is formed of a stainless steel material.

7. The method of claim 5 wherein the bend angle $\Theta$ is between 15 degrees and 45 degrees in the resting state.

8. The method of claim 5 wherein the distal region has a length after the bend $L_{ab}$ that is between 0 mm and 25 mm.

9. The method of claim 5 wherein at least the distal region is formed of an elastic material including at least one of a metal and a metal alloy.

10. The method of claim 5 wherein the offset $d_{off}$ is measured perpendicularly between a first line, extending parallel to the proximal region longitudinal axis, and a second line that is parallel to the first line, the first line including the distal end of the working feature and the second line extending along an upper surface of the proximal region having a greatest distance from the distal end in a direction normal to the proximal region longitudinal axis.

11. The method of claim 5 wherein the distal region is established by a first hollow tube that extends proximally as a proximal section at least partially into the proximal region, and the proximal region is established by a second hollow tube placed coaxially over the proximal section of the first tube.

12. The method of claim 5 wherein the shaft is monolithic and the distal region is formed by removal of shaft material in the distal region.

13. The method of claim 5 wherein the distal region of the surgical waveguide conduit tool has an elastic modulus E within a range from 193 GPa inclusive to 195 GPa inclusive.

14. A surgical waveguide conduit tool, comprising:
a shaft including:
a rigid proximal region having a length $L2$ along a proximal region longitudinal axis, the rigid proximal region including a proximal lumen, and having a first cross-sectional perimeter that is perpendicular to the proximal region longitudinal axis; and
a distal region coupled to the proximal region and having a length $L1$ measured in a direction parallel to the proximal region longitudinal axis, the distal region including a distal lumen communicatively coupled to the proximal lumen, the proximal lumen and the distal lumen sized to receive an optical waveguide, if any, therethrough, the distal region having a second cross-sectional perimeter that is perpendicular to the proximal region longitudinal axis, the second cross-sectional perimeter being less than the first cross-sectional perimeter, the distal region including an integral working feature and having a bend located between the working feature and the proximal region, the working feature having a rounded distal tip and an opening that has an opening perimeter that is greater than the second cross-sectional perimeter of the distal region, the opening defines an S-shaped curve including a first curve having a first orientation of curvature and a second curve having a second orientation of curvature that is opposite to the first orientation of curvature.

15. The surgical waveguide conduit tool of claim 14 wherein the rigid proximal region has an outer diameter $D_2$, and the distal region has an outer diameter $D_1$ that is less than $D_2$.

16. The surgical waveguide conduit tool of claim 14 wherein the distal region has an elastic modulus E within a range from 193 GPa inclusive to 195 GPa inclusive.

17. The surgical waveguide conduit tool of claim 15 wherein the bend has a bend angle $\Theta$ that is greater than 10 degrees in a resting state, the distal region has a length after the bend $L_{ab}$, the shaft has a total access length of $L1+L2$, the distal region has an offset $d_{off}$ relative to the proximal region where $d_{off}$ is greater than $D_2$, and the working feature is insertable through an access device, if any, having an inner diameter $D_3$ that is smaller than the offset $d_{off}$ of the distal region.

18. The surgical waveguide conduit tool of claim 17 wherein offset $d_{off}$ is greater than $(1.5)(D_2)$ and at least the distal region of the shaft is formed of a stainless steel material.

19. The surgical waveguide conduit tool of claim 17 wherein offset $d_{off}$ is greater than $(2)(D_2)$.

20. The surgical waveguide conduit tool of claim 17 wherein the bend angle $\Theta$ is between 15 degrees and 45 degrees in the resting state and at least the distal region of the shaft is formed of a stainless steel material.

21. The surgical waveguide conduit tool of claim 17 wherein the length after the bend $L_{ab}$ is between 0 mm and 25 mm.

22. The surgical waveguide conduit tool of claim 17 wherein the offset $d_{off}$ is measured perpendicularly between a first line, extending parallel to the proximal region longitudinal axis, and a second line that is parallel to the first line, the first line including the distal end of the working feature and the second line extending along an upper surface of the proximal region having a greatest distance from the distal end in a direction normal to the proximal region longitudinal axis.

23. The surgical waveguide conduit tool of claim 17 wherein the access device, if any, is selected to be a trocar having the inner diameter $D_3$ and the offset $d_{off}$ of the distal region being greater than diameter $D_3$, and at least 30% of the bend is retained during the advancement of the tool through the trocar, if any, using less than 10 N of force.

24. The surgical waveguide conduit tool of claim 23 in combination with the trocar.

25. The surgical waveguide conduit tool of claim 24 further including the optical waveguide and wherein the offset $d_{off}$ is at least 1.5 times as large as diameter $D_3$ and at least the distal region of the shaft is formed of a stainless steel material.

26. The surgical waveguide conduit tool of claim 25 wherein the bend angle Θ is between 15 degrees and 45 degrees in the resting state.

27. The surgical waveguide conduit tool of claim 14 wherein at least the distal region is formed of an elastic material including at least one of a metal and a metal alloy.

28. The surgical waveguide conduit tool of claim 14 wherein the distal region is established by a first hollow tube that extends proximally as a proximal section at least partially into the proximal region, and the proximal region is established by a second hollow tube placed coaxially over the proximal section of the first tube.

29. The surgical waveguide conduit tool of claim 14 wherein the shaft is monolithic and the distal region is formed by removal of shaft material in the distal region.

* * * * *